(12) United States Patent
Mercolino et al.

(10) Patent No.: US 11,676,693 B2
(45) Date of Patent: Jun. 13, 2023

(54) INTEGRATED DEVICE AND SYSTEM FOR DRUG DISPENSING

(71) Applicant: Verinetics, Inc., Research Triangle Park, NC (US)

(72) Inventors: Thomas J. Mercolino, Chapel Hill, NC (US); John Gerard McKeon, Killarney (IE); Colin Daniel Zico O'Dowd, Cary, NC (US); Matthew Hanlon, Durham, NC (US)

(73) Assignee: Verinetics, Inc., Research Triangle Park, NC (US)

( * ) Notice: Subject to any disclaimer, the term of this patent is extended or adjusted under 35 U.S.C. 154(b) by 0 days.

(21) Appl. No.: 17/245,028

(22) Filed: Apr. 30, 2021

(65) Prior Publication Data

US 2021/0249112 A1    Aug. 12, 2021

Related U.S. Application Data

(63) Continuation-in-part of application No. PCT/US2019/058967, filed on Oct. 30, 2019.

(60) Provisional application No. 62/752,392, filed on Oct. 30, 2018.

(51) Int. Cl.
| | |
|---|---|
| *G16H 20/13* | (2018.01) |
| *A61J 7/00* | (2006.01) |
| *G16H 40/67* | (2018.01) |
| *G16H 40/63* | (2018.01) |
| *A61J 1/03* | (2023.01) |
| *A61J 7/04* | (2006.01) |

(52) U.S. Cl.
CPC .............. *G16H 20/13* (2018.01); *A61J 1/03* (2013.01); *A61J 7/0053* (2013.01); *A61J 7/0084* (2013.01); *A61J 7/04* (2013.01); *G16H 40/63* (2018.01); *G16H 40/67* (2018.01); *A61J 2200/30* (2013.01)

(58) Field of Classification Search
CPC ........ G16H 20/13; G16H 40/67; G16H 40/63; A61J 1/03; A61J 7/0053; A61J 7/04; A61J 7/0084; A61J 2200/30
See application file for complete search history.

(56) References Cited

U.S. PATENT DOCUMENTS

| | | | |
|---|---|---|---|
| 351,167 A * | 10/1886 | Diehl | H01R 39/04 310/236 |
| 4,753,352 A | 6/1988 | Dauphin et al. | |
| 4,953,745 A | 9/1990 | Rowlei, Jr. | |

(Continued)

FOREIGN PATENT DOCUMENTS

| | | |
|---|---|---|
| CA | 2814259 A1 | 3/2001 |
| JP | 2002279068 A | 9/2002 |

(Continued)

OTHER PUBLICATIONS

ISA/RU, International Search Report and Written Opinion for International Patent Application No. PCT/US2019/058967, dated Feb. 13, 2020, 10 pages.

(Continued)

*Primary Examiner* — Michael Collins
(74) *Attorney, Agent, or Firm* — NK Patent Law

(57) ABSTRACT

A device includes a reservoir for holding an article that has thereon and a dispenser for dispensing the articles from the reservoir. A deactivation mechanism may deactivate medicament held within the reservoir.

11 Claims, 11 Drawing Sheets

(56) References Cited

U.S. PATENT DOCUMENTS

Figures 1, 2:
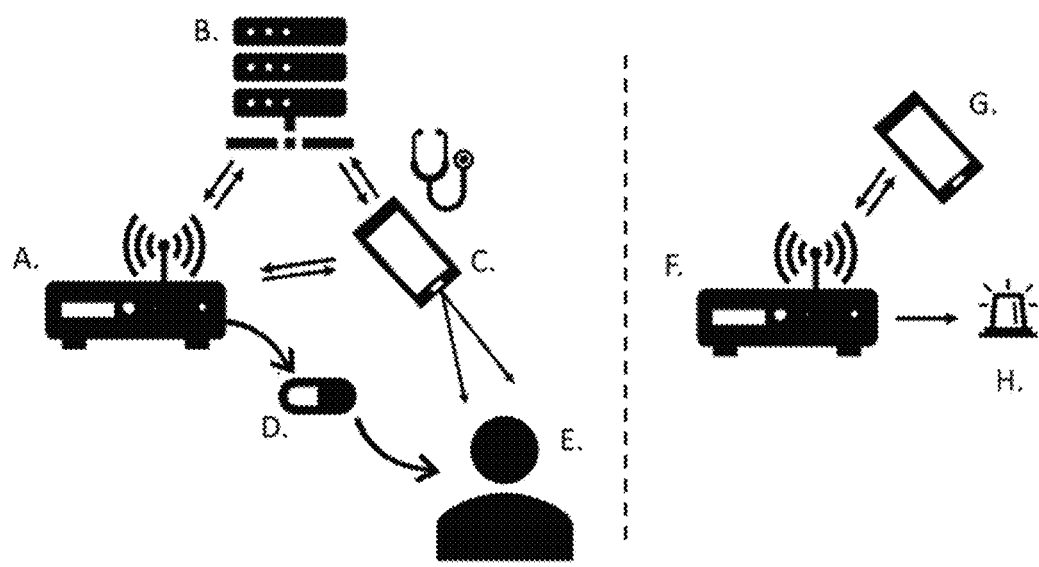

| | | | | |
|---|---|---|---|---|
| 5,971,594 | A * | 10/1999 | Sahai | A61J 7/0481 |
| | | | | 221/9 |
| 6,799,572 | B2 | 10/2004 | Nichols et al. | |
| 7,118,007 | B1 * | 10/2006 | Yates | G07F 17/0092 |
| | | | | 221/133 |
| 8,108,068 | B1 * | 1/2012 | Boucher | G01G 17/00 |
| | | | | 700/240 |
| 9,150,346 | B1 * | 10/2015 | Aramian | A61J 7/04 |
| 9,889,069 | B1 * | 2/2018 | Coe | A61J 7/0084 |
| 10,073,954 | B2 * | 9/2018 | Chen | B65B 5/106 |
| 10,426,707 | B2 | 10/2019 | Hsu | |
| 10,521,560 | B2 | 12/2019 | Bossi et al. | |
| 10,597,206 | B2 | 3/2020 | Corey et al. | |
| 10,821,054 | B1 * | 11/2020 | Howton | A61J 7/0481 |
| 11,246,805 | B2 * | 2/2022 | Chen | B65B 57/14 |
| 2007/0023444 | A1 | 2/2007 | Holloway et al. | |
| 2009/0294521 | A1 | 12/2009 | de la Huerga | |
| 2011/0226817 | A1 * | 9/2011 | Ortenzi | A61J 1/18 |
| | | | | 222/424.5 |
| 2011/0240511 | A1 | 10/2011 | Bolton et al. | |
| 2012/0277514 | A1 | 11/2012 | Uhland et al. | |
| 2013/0090594 | A1 * | 4/2013 | Palmer | A61J 7/0445 |
| | | | | 604/60 |
| 2013/0110283 | A1 * | 5/2013 | Baarman | A61J 7/0084 |
| | | | | 700/236 |
| 2016/0158107 | A1 * | 6/2016 | Dvorak | A61J 7/0007 |
| | | | | 221/9 |
| 2018/0285880 | A1 | 10/2018 | Jerstroem et al. | |
| 2020/0279632 | A1 * | 9/2020 | Mercolino | A61J 7/0084 |

FOREIGN PATENT DOCUMENTS

| | | |
|---|---|---|
| WO | 2003035030 A1 | 5/2003 |
| WO | 2009048848 A1 | 4/2009 |

OTHER PUBLICATIONS

WIPO, International Preliminary Report on Patentability for International Patent Application No. PCT/US2019/058967, dated Apr. 27, 2021, 8 pages.

USPTO, Non-Final Office Action for corresponding U.S. Appl. No. 16/829,043, dated Jul. 16, 2020, 7 pages.

USPTO, Final Office Action for corresponding U.S. Appl. No. 16/829,043, dated Oct. 27, 2020, 9 pages.

* cited by examiner

Left Panel        Center Panel        Right Panel

Left Panel        Center Panel        Right Panel

Top Left Panel

Top Right Panel

Bottom Left Panel

Bottom Right Panel

Top Left Panel

Top Right Panel

Bottom Left Panel

Bottom Right Panel

Left Panel     Right Panel

Upper Panel

Lower Panel

INTEGRATED DEVICE AND SYSTEM FOR DRUG DISPENSING

CROSS-REFERENCE TO RELATED APPLICATIONS

This application claims priority to PCT Patent Application No. PCT/US2019/058967 filed on Oct. 30, 2019, which claims priority to U.S. Provisional Patent Application No. 62/752,392 filed on Oct. 30, 2018, the entire contents of which are incorporated by reference herein.

TECHNICAL FIELD

The present invention relates to compositions, systems, methods, and devices for medications adherence, improving the quality while reducing the cost of clinical trials, for reliably deterring CS drugs' diversion, making them safer from abuse, and for integrating wearable devices and blockchain data management in said systems and methods.

BACKGROUND

Medications adherence (sometimes referred to as "Medications compliance") is the degree to which a patient correctly follows medical advice, usually with respect to prescribed pharmaceutical therapies. Patient's or health care provider's failures in medications adherence are a major obstacle to the effective delivery of health care. Higher cost for medication is inversely related to medication adherence. In order to manage medication costs, patients fail to fill their prescription, skip or reduce doses. Other barriers to compliance include the complexity of modern medication regimens, poor "health literacy" and not understanding treatment benefits, occurrence of undiscussed side effects, poor treatment satisfaction, cost of prescription medicine, and poor communication or lack of trust between a patient and his or her health-care provider.

Efforts to improve compliance have been aimed at simplifying medication packaging, providing effective medication reminders, and improving patient education. A wide variety of packaging approaches have been proposed to help patients complete prescribed treatments. These approaches include formats that increase the ease of remembering the dosage regimen as well as different labels for increasing patient understanding of directions. For example, medications are sometimes packed with reminder systems for the day and/or time of the week to take the medicine.

Emerging practice of telemedicine technology is expected to improve physicians' capabilities to remotely monitor patients in real-time and to communicate recommendations and medication adjustments using personal mobile devices, such as smartphones, rather than waiting until the next office visit.

Medications adherence may be improved through event monitoring systems, as in the form of smart medicine bottle tops, smart pharmacy vials or smart blister packages work without any patient input, and record the time and date the bottle or vial was accessed, or the medication removed from a blister package.

There remains significant needs to offer simplified devices and methods for medications adherence that integrate improvements to packaging, effective medication reminders, patient education. Moreover, such improvements should address unmet needs in integrating further with event management systems and the emerging practices of telemedicine.

Clinical trials required to obtain regulatory approvals for new medications are designed to test hypotheses and rigorously monitor and assess outcomes. The test design is specified in a document called a clinical trial protocol. The protocol is intended to ensure that all researchers perform the trial in the same way on similar subjects and that the data is comparable across all subjects. By extension, the adherence or compliance of subjects to the study protocol is critically important to any clinical trial's success.

There are two goals in clinical trials: to learn whether a medication has sufficient benefit to outweigh its risks, called "safety"; and to assess a medication's efficacy or effectiveness. Both safety and efficacy are evaluated relative to how the treatment is intended to be used, what other treatments are available, and the severity of the disease or condition.

Safety studies are typically conducted using presumptively healthy volunteers as subjects. The goals of the safety study are to determine acute side effects in the dosing range expected to be relevant in achieving efficacy by the medication. A side effect is an effect, typically adverse, that is secondary to the one intended. Because no two people are exactly the same, even drugs that have virtually no side effects in the population as a whole might have significant side effects in a rare few.

Efficacy testing in clinical trials involves with specific health conditions who are willing to try an experimental treatment. During the trial, investigators follow the trial protocol to recruit subjects with the specified characteristics, administer the treatment(s) and collect data on the subjects' health. These data include measurements such as vital signs, concentration of the study drug in the blood or tissues, changes to symptoms, and whether improvement or worsening of the condition targeted by the study drug occurs. The researchers send the data to the trial sponsor, who then analyzes the pooled data using statistical tests.

In many clinical trials certain subjects will be given an experimental or "test" drug, while another experimental control group is given either a standard treatment (sometimes called a "comparator drug") for the illness or an inactive placebo. In a clinical trial any change in the placebo arm is known as the placebo response, and the difference between this and the result of no treatment is the placebo effect.

For the control group to provide comparative basis for assessing effects of the test treatment, subjects must be matched for age, sex, severity of illness, and other criteria as may be relevant. The number of subjects in each group is driven by statistical sampling requirements needed to detect differences among the groups and subgroups.

Trial subjects are assigned to test or control groups randomly. In most clinical trials, the subjects and the research team are "double-blinded" to which subject is in which group to minimize bias in reporting or trial conduct. Moreover, the test drug and comparator drug or placebo can be made to resemble each other to prevent the subjects or research team from knowing how each subject has been assigned, as expectations about efficacy can influence results. The study protocol specifies when "unblinding" may occur, at which point results are associated with each subject sorted by test and control group.

Clinical trials based upon statistical comparison between test group and control may fail to adequately quantitate placebo effects or differences from a comparator drug because of factors including: natural recovery from or fluctuation in symptoms; subjects receiving additional, uncontrolled treatments; response bias from subjects, e.g., scaling bias; and reporting bias from experimenters. There remains significant needs to offer simplified devices and methods that will overcome these inadequacies yet reduce overall cost of clinical trials.

Wearable technology can monitor a user's health and collect corresponding data, such as: heart rate, calories burned, steps walked, blood pressure, release of biochemicals or metabolic markers to sweat, and time spent exercising. Wearable technology has the potential to be extended to measuring blood alcohol content, monitoring of patients via an electrocardiogram, and more general health risk assessment of well-being or frailty. Wearable technology can also collect biometric data such brainwaves (EEG), and muscle bio-signals (EMG). These functions are often bundled together in a single unit, like an activity tracker or a smartwatch that may also provide correlated information about the user's GPS location or connection to a wireless network. Despite advances in wearable technology, there remains unmet need for integrating wearable devices in drug dispensing as part of patient medication adherence and for subject protocol adherence in clinical trials. In each case, there is a need that the data collected through the wearable be an indicator for drug effects.

Medical patient or clinical trials subject data records often contain personally identifiable information (PID) such as names, social security numbers and home addresses. For patient medical health records, blockchain technology puts PID under control of the patient rather than a third party, through the patients' private and public keys. Patients could then control access to their health records, making transferring information easier yet more secure with respect to PID. Health information and PID is difficult or impossible to delete or be tampered when maintained on blockchain. Moreover, each transaction would be timestamped and could include useful position information about the correlated data.

Narcotic analgesics and other controlled substances (CS drugs) are subject to restrictions on distribution, dispensing, and disposal. Included in the most restrictive Schedule II category are narcotic analgesics, prescriptions for which must be written and signed by the practitioner and may not be refilled. Accordingly, while there is a need to address integrating the benefits of wearables, blockchain, and monitored administration of drugs generally, these needs are more acute with respect to CS drugs.

Abuse of narcotic analgesics and other controlled substances (CS drugs) has increased in recent years, leading to over 33,000 deaths per year, about half of which are attributable to prescription opioid abuse. Alarmingly, while the US accounts for only 4.6% of the world population, it consumes 80% of all opioids produced. Widespread prescription opioid analgesics use contributes to the elevated prevalence of opioid addiction, CS diversion and other criminal activities, CS abuse, and CS overdoses and deaths. In the U.S., in the period from 2001 through 2008, reports to the US Department of Justice's Drug Enforcement Agency (DEA) involving hydrocodone increased 201%, and those for morphine and oxycodone increased 197% and 178%, respectively. According to the 2007 National Survey on Drug Use and Health, an estimated 7% of adolescents and 5% adults (roughly 13 million people, total), used prescription pain relievers for nonmedical reasons during the prior year. More than 1 in 10 high school seniors report abusing VICODIN and/or OXYCONTIN; 54% report that prescription narcotics obtained for nonmedical use came from a friend or relative. Another area of concern is addiction and abuse in elderly patients and drug diversion from them by friends or relatives.

In the US, the decision to require a prescription for a pharmaceutical product is the US Food and Drug Administration's (FDA's). Additionally, however, the under the authority of The Controlled Substances Act places all pharmaceuticals products into one of five schedules. Pharmaceuticals are scheduled as a CS if they have "potential for abuse", as indicated by: evidence that individuals are taking the drug such that it is a hazard to themselves or others; significant diversion from legitimate drug channels; individuals taking the drug without medical advice; or, a new drug with similar pharmacology to a drug having abuse potential.

Prescription CS drugs are subject to additional restrictions. Included in the most restrictive Schedule II category are narcotic analgesics, prescriptions for which must be written and signed by the practitioner and may not be refilled.

In addition to DEA, FDA has made efforts toward ensuring that the benefits of drugs with abuse potential outweigh their risk. The FDA Amendments Act of 2007 (FDAAA) authorized FDA to require pharmaceutical manufacturers to comply with Risk Evaluation and Mitigation Strategy (REMS), the exact nature of which remains to be seen, but will likely include post-marketing studies and clinical trials and safety-related labeling changes. FDA states that they are focusing their attention for REMS implementation on narcotic analgesics and methods that will assure their safe and effective use in the legitimate treatment of pain. Regarding these objectives, FDA states that it is seeking broad participation and input to find ways to reduce abuse, misuse, addiction, overdose, and death, yet maintain access to these essential medications. A REMS "package" will be required for approval of all new narcotic analgesics. This requirement will be applied retroactively to previously approved drugs in this class, both branded and generic.

Current package-level security measures are inadequate to deter diversion of drugs with abuse potential, since once unpackaged the chain of custody for the drug and related security measures are no longer maintained. Current technologies provide no clear solution to achieve these objectives. Therefore, the goal of this application is to configure and demonstrate proof-of-concept for an integrated, end-to-end system for deterring opioid or CS theft in the hospital setting, while making tracking disposal of unused CS doses safer and more efficient.

Proprietary codes like TRAXSECUR enable valid, registered unique identifiers to be embedded in machine-readable marks. Such codes address the risks of open-format product identification labeling systems by making it virtually impossible for fraudsters to generated valid, registered unique identifiers embedded in machine-readable marks, nor to unlawfully obtain one mark on a product and attempt to either modify that product or move the mark (e.g. by copying) to a different product. Proprietary codes may also provide a way to quickly and easily verify that different, independent identifiers on the same product are properly correlated with one another according to the way they were created when the packing was originally produced.

Medicated-Assisted Treatment (MAT) is the use of FDA-approved medications, in combination with counseling and behavioral therapies, to provide a "whole-patient" approach to the treatment of substance use disorders. Two medications (methadone and buprenorphine) commonly used to treat opioid addiction are CS drugs, themselves. It is desirable and sometimes required by law that the license medical practitioner who provides MAT do so in a "qualified practice setting." A qualified practice setting is one that ideally provides: professional coverage for patient medical emergencies during hours when the practitioner's practice is closed; access to case-management services for patients including referral and follow-up services, such as medical, behavioral, social, housing, employment, educational, or other related services; uses health information technology systems such as electronic health records; and, is registered for their US State prescription drug monitoring program (PDMP) where operational and in accordance with US Federal and State law. It is even more desirable that access to outpatient care, including in home settings, qualify for some or all of the ideal aspects of a qualified practice setting given above. Accordingly, there remains a need to address these disadvantages and others not described herein.

SUMMARY

The present invention relates to compositions, systems, methods, and devices for medications adherence, improving the quality while reducing the cost of clinical trials, for reliably deterring CS drugs' diversion, making them safer from abuse, and for integrating wearable devices and blockchain and distributed data management in the systems and methods.

The present disclosure describes on-dose authentication as part of a system comprised of a reusable dispensing device with networked communication capabilities. In certain embodiments, the device communicates with central hospital information systems and healthcare workers authorized to manage a specified patient. In other embodiments, the device communicates with clinical trials information systems to manage a specified subject's compliance with a clinical trial protocol.

In some embodiments, the compositions, systems, methods, and devices of the present invention are components in a Controlled Substance Diversion Prevention Program (CSDPP). The device would monitor administration of CS drug to a patient and acts as a deterrent to CS drugs' diversion, making them safer from abuse. To achieve this benefit, the CSDPP device or system (which is referred to as "CSDPP device" throughout) may be fitted with a disposable cartridge that would track the identity and utilization of individual CS doses that will carry a unique identifier (UID). The device also monitors deactivation of unused doses, wherein their identity and quantity is efficiently synchronized with pre-existing data records. The device is designed to monitor disposal of wasted CS doses. If CS doses are separated from their home device, the UID can be read with an application on a mobile phone, which provides a strong deterrent to diversion before it occurs.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

FIG. 1 illustrates the CSDPP device (A) as a secure container for CS doses. The device communicates with the hospital information technology (HITS) system (B). An HCW authorized to administer the CS drug (C) initiates the process for dispensing a dose. The device dispenses a dose (D) to the patient (E). A CSDPP device out of its "home" network (F.) communicates its status the its authorized HCW (G) who may override CS the device's automatic notification to law enforcement (H).

Figure 3:
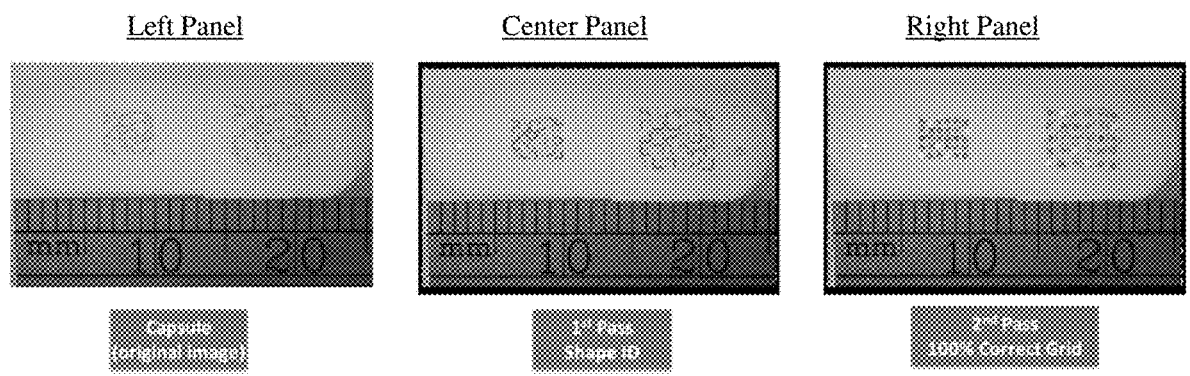

FIG. 1 illustrates a diagram of the system described in the present disclosure;

FIG. 2 illustrates a series of images that depict a complex numerical unique identifier, conversion of the complex UID if 2A into a reference character string according to the rubric that associates each reference character with a different integer, a mark created from the reference character string of 2B, wherein the reference characters are constrained to a six by six reference characters field, and a mark created as a border for content using the reference character string of 2B, wherein the reference characters are constrained to a sixteen reference character-wide by eight reference character high field and where the null character encoded by the digit 9 has been inserted in the string. Such borders are useful when configured as a feature on a tamper evident seal;

FIG. 3—LEFT, a gelatin capsule marked with TraxSecur codes (see FIG. 2 and its description for more) taken at low magnification and an otherwise mobile, one occupying roughly less than 4 square mm and the other roughly 6 square mm CENTER: Output from TraxSecur analysis software first pass showing that all shapes are properly identified and; and RIGHT: Output from TraxSecur analysis software showing that the TraxSecur grid has been determined, a demonstration that the software functions as intended in reading codes printed on the millimeter scale.

Figure 4:
Figure 5:
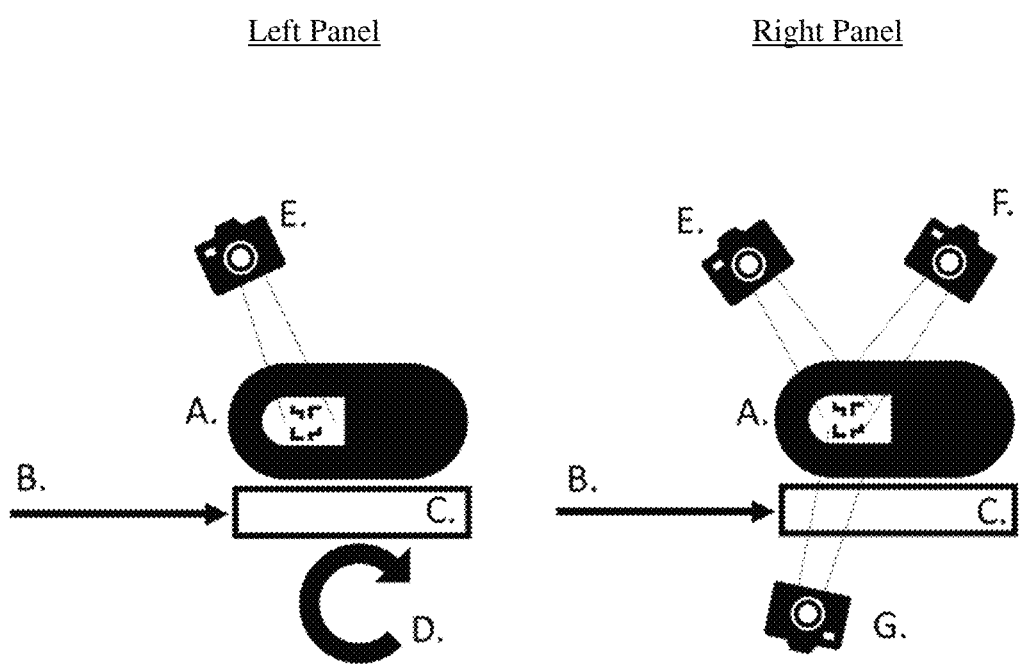

FIG. 4—TraxSecur, a product described herein, can be configured as a pre-printed tamper seal for application to each of the DispenSecur drug container cartridge;

FIG. 5—A representative reading mechanism and alternative processes therefor, as further described in Example 1, below FIG. 6—A flow chart detailing the logic behind CSDPP device operation in the hospital setting illustrating the features and process that provide a deterrent to diversion or theft of CS doses. Details are found in Example 2, below.

Figure 7:
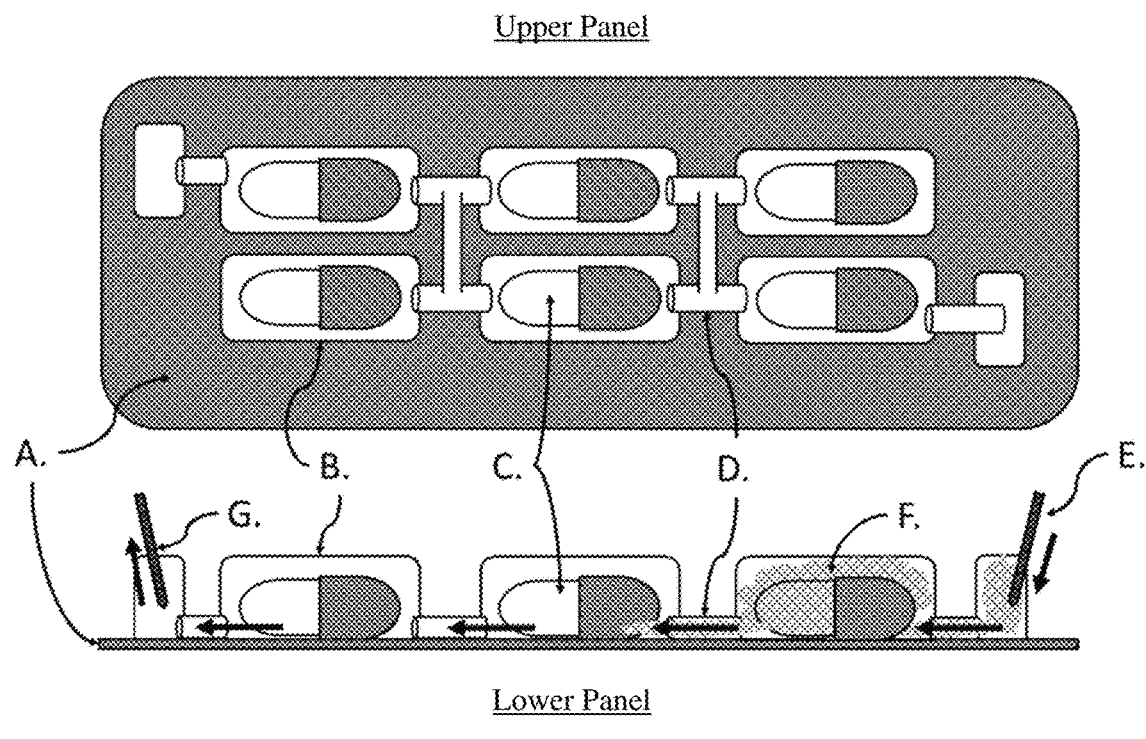

FIG. 7—A representative cartridge for holding capsules for illustration, as also further described in Example 2, below FIG. 8—A flow chart of device operation in the clinical trial setting. Details are found in Example 3, below.

Figure 9:
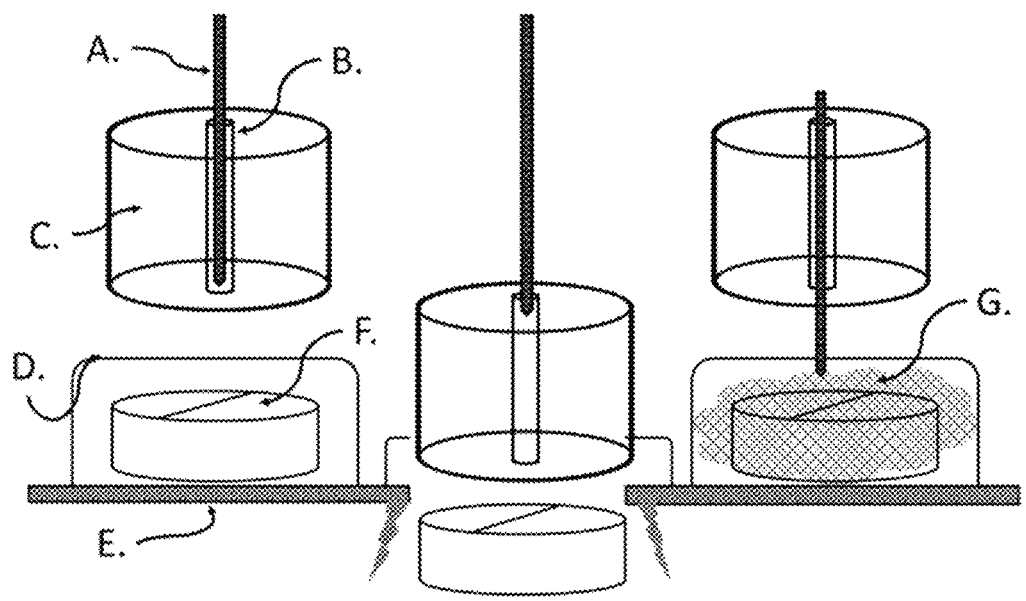

FIG. 9—A representative dispensing mechanism using tablets for illustration, as also further described in Example 3, below FIG. 10—A representative cartridge for holding articles to be dispensed from the device of this invention, and further shows a mechanism and process for deactivating articles remaining in the device, as further describe in Example 4, below FIG. 11—A representative dispensing mechanism using a tablet cartridge, as also further described in Example 5.

Figure 12:
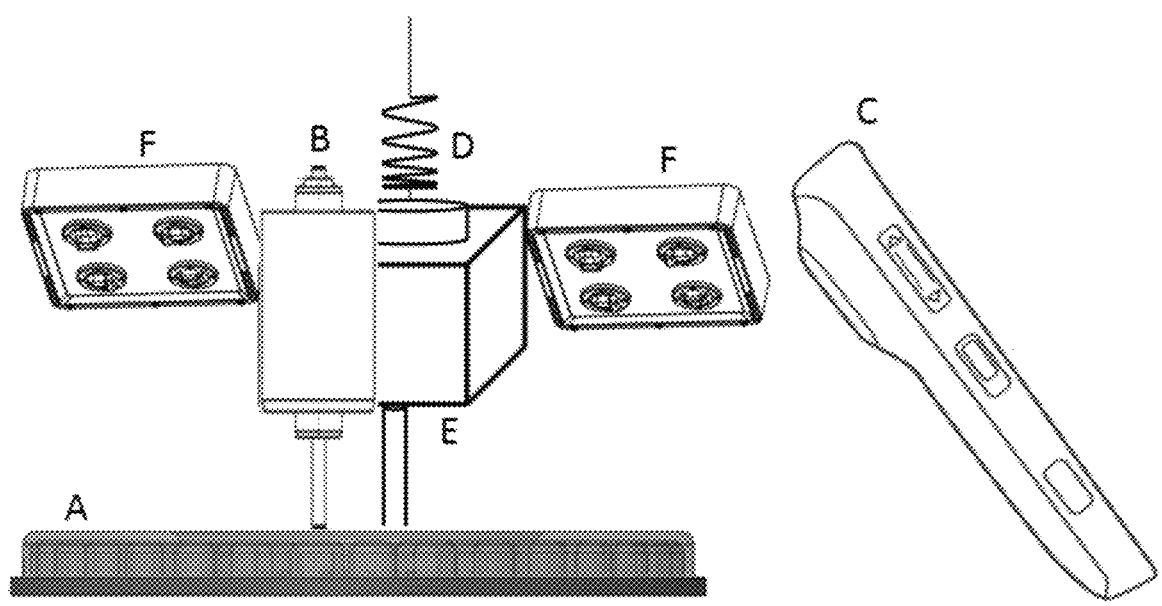

FIG. 12—A representative dispense and deactivation system using a rotary tablet cartridge and UV curing, as also further described in Example 5.

Figure 13:
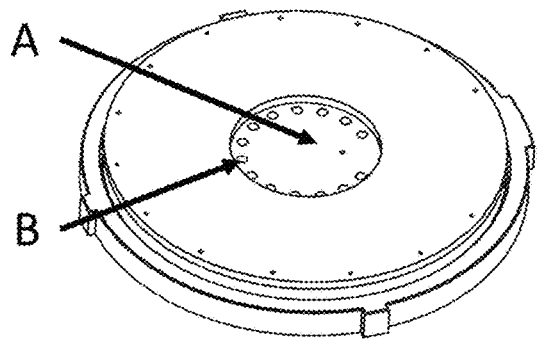
Figure 13:
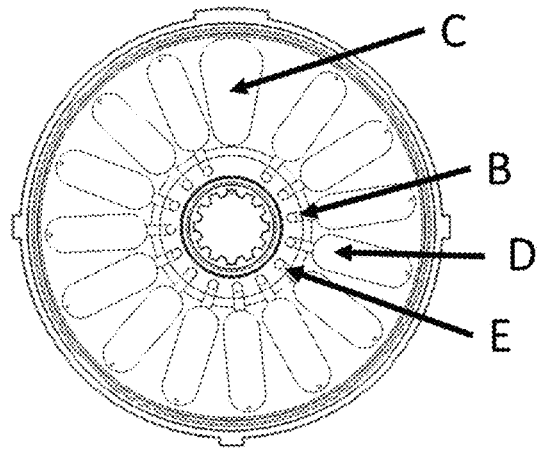
Figure 13:
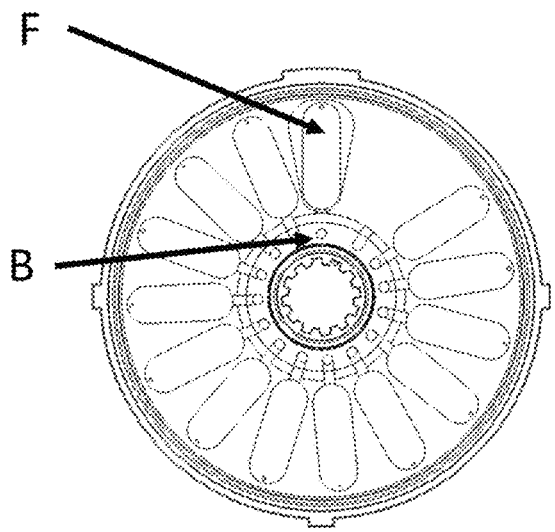
Figure 13:
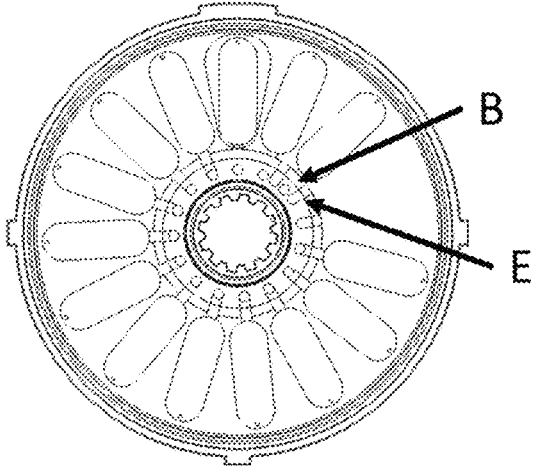

FIG. 13—A representative deactivation system using a rotary tablet cartridge, wherein the deactivation liquid only is directed into full, but not spent, cartridge locations, as also further described in Example 5.

Figure 14:
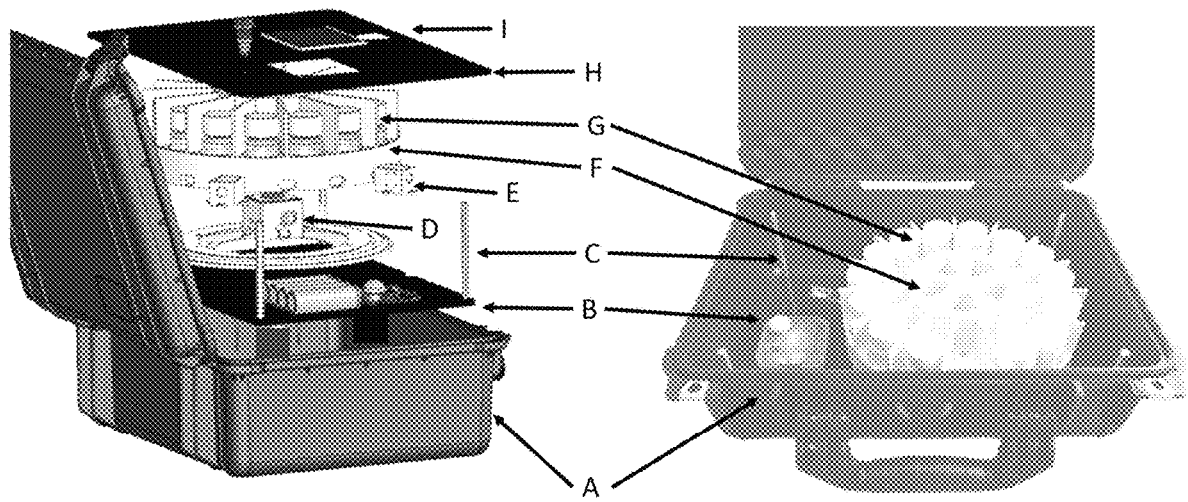

FIG. 14—Exploded and assembled views of a representative dispensing mechanism using a rotary carousel that holds vials, as further described in Example 6.

Figure 15:
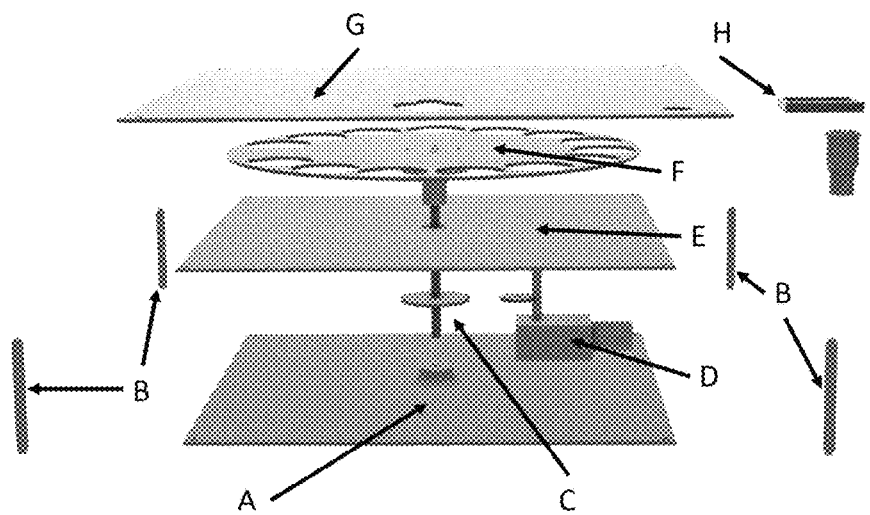

FIG. 15—An exploded view of a representative dispensing mechanism using an a substantially flat rotary carousel that holds vials, as also further described in Example 6.

Figure 16:
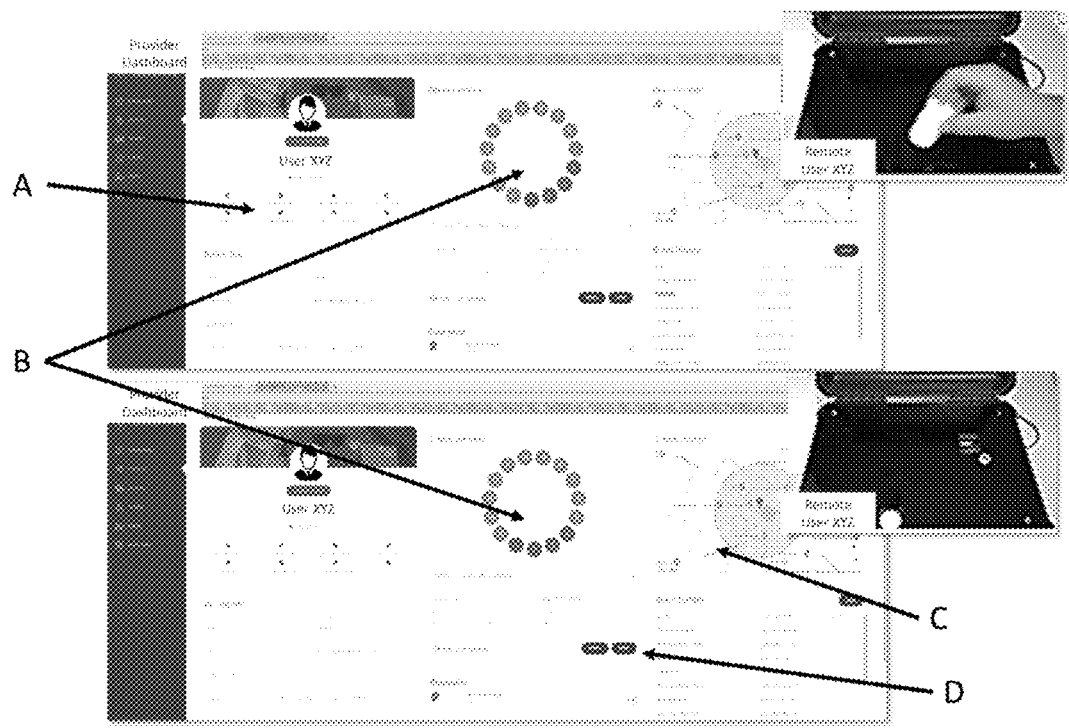

FIG. 16—A representative system comprised of a dispensing mechanism remotely monitored on a dashboard, as alsp further described in Example 6.

Figure 17:
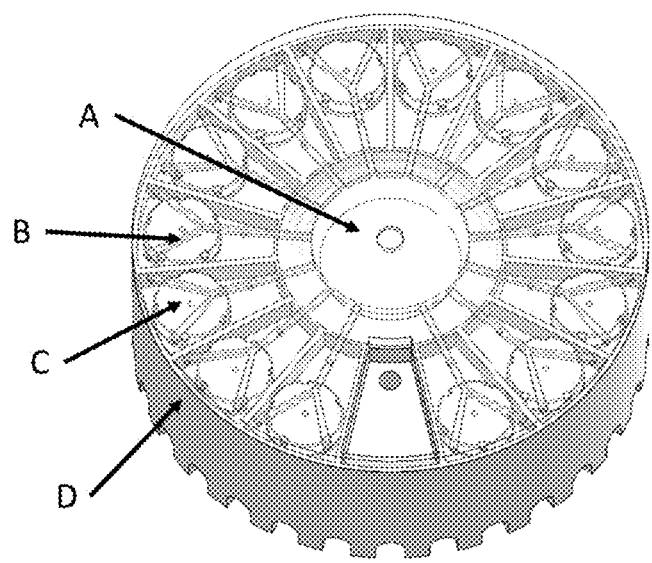

FIG. 17—A representative deactivation system using a rotary vial carousel, as further described in Example 6.

DETAILED DESCRIPTION

The present disclosure is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" is used herein to connote different aspects of methods employed, the term should not be interpreted as implying any particular order among or between various steps herein disclosed unless and except when the order of individual steps is explicitly described.

As referred to herein, the term "computing device" should be broadly construed. Examples would include a smart phone, a cell phone, a pager, a personal digital assistant (PDA, e.g., with GPRS NIC), a mobile computer with a cellular radio, or the like. A typical computing device is a wireless data access-enabled device (e.g., an iPHONE® smart phone, a BLACKBERRY® smart phone, a NEXUS ONE™ smart phone, an iPAD™ device, or the like) that is capable of sending and receiving data in a wireless manner using protocols like the Internet Protocol, or IP, and the wireless application protocol, or WAP. This allows users to access information via wireless devices, such as smart phones, mobile phones, pagers, two-way radios, communicators, and the like. Wireless data access is supported by many wireless networks, including, but not limited to, CDPD, CDMA, GSM, PDC, PHS, TDMA, FLEX, ReFLEX, iDEN, TETRA, DECT, DataTAC, Mobitex, EDGE and other 2G, 3G, 4G and LTE technologies, and it operates with many handheld device operating systems, such as PalmOS, EPOC, Windows CE, FLEXOS, OS/9, JavaOS, iOS and Android. Typically, these devices use graphical displays and can access the Internet (or other communications network) on so-called mini- or micro-browsers, which are web browsers with small file sizes that can accommodate the constrained operating environment of wireless devices on wireless networks. In a representative embodiment, the computing device is a cellular telephone or smart phone that operates over GPRS (General Packet Radio Services), which is a data technology for GSM networks. In addition to a conventional voice communication, a given computing device can communicate with another such device via many different types of message transfer techniques, including SMS (short message service), enhanced SMS (EMS), multi-media message (MMS), email WAP, paging, or other known or later-developed wireless data formats. Although many of the examples provided herein are implemented on a computing device, the examples may similarly be implemented on any suitable "computing device". An imaging device is any computing device operable to take or receive image data.

As used herein, an article is a physical object on which a label may be applied. Examples of articles would include a capsule, a solid oral dosage form, a prefilled syringe, shipping boxes, vehicles, personal property, electronics, etc.

As used herein, a vial is an article that may be used to hold a physical object, a plurality of physical objects, or a liquid. A vial may be capped or otherwise sealed, uncapped or unsealed. "Vials" also may be removable cups whether capped, sealed, or unsealed.

As used herein, a pharmaceutical may be a drug used to diagnose, cure, treat, or prevent disease in a human or animal.

As used herein, a nutraceutical may be a food or a substance in food, which is used in healthcare or as a dietary supplement.

As used herein, a recreational drug may be a legal drug (such as *cannabis*) used without medical justification.

As used herein, a label may include machine detectable information affixed to an article. A mark may be applied to an article through several different means including printing on the article or affixing a label to an article. A mark may be visible to the human eye, or invisible but machine readable, as in the case of magnetic ink.

As used herein, a mark may include a label that may be embedded with an authorization code. Authorization codes are selected to be unique, and unique identify the article within the disclosed system. A mark may be applied to an article through several different means including printing on the article or affixing a label to an article. A mark may be visible to the human eye, or invisible but machine readable, as in the case of magnetic ink.

As used herein, an authentication code may be any appropriately configured code, including a random code of assigned variables. The code may be any of the codes illustrated in patent application Ser. No. 13/457,115 filed on Apr. 26, 2012 by a common inventor of this disclosure and application Ser. No. 14/067,945 filed on Oct. 30, 2013, the entire contents relating to the types of code, methods for imaging, methods for generating, and methods for creating a signature are incorporated by reference herein.

As used herein, a signature may be a numerical signature determined from the authorization code. In some embodiments, the signature is a numerical signature.

As used herein, a unique identifier may be any identifier that may be unique within the disclosed system. An example of a unique identifier is an authorization code.

As used herein, a barcode is an optical, machine-readable, representation of data; the data usually describes something about the object that carries the barcode. Originally barcodes systematically represented data by varying the widths and spacing of parallel lines, and is referred to as linear or one-dimensional (1D). Later two-dimensional (2D) codes were developed, using rectangles, dots, hexagons and other geometric patterns in two dimensions, usually called barcodes although they do not use bars as such. Characteristic of barcode technologies is that each position carries just two bits of information, i.e., a location is black (1) or white (0).

As used herein, a tamper evident seal is seals where it is possible to detect if the seal has been opened or tampered with. As used herein the tamper evident seal may contain an embedded security thread.

The unique identifiers embedded in machine-readable marks may be any appropriately configured code, including a random code of assigned variables. The code may be any of the codes illustrated in U.S. Pat. Nos. 9,052,336, 10,044, 704, U.S. patent application Ser. No. 15/935,708 or the printed codes of U.S. Pat. Nos. 7,874,489 and 8,458,475. the entire contents relating to the types of codes, methods for imagining, methods for generating, and methods for creating a signature are incorporated by reference herein.

A system of the present invention may include one of a dispensing Controlled Substance Diversion Prevention Program (CSDPP) device that communicates with central hospital information systems and healthcare workers authorized to manage a specified patient. In preferred embodiments the device may be reusable. The device also would monitor administration of CS drug to that patient. The CSDPP device may be fitted with a disposable cartridge that would track the identity and utilization of individual CS doses that carry a unique identifier (UID). The device also monitors deactivation of unused doses wherein their identity and quantity may be efficiently synchronized with pre-existing data records. The device may be designed to monitor disposal of wasted CS doses. If CS doses are separated from their home device, the UID may be read with an application on a mobile phone, which provides a strong deterrent to diversion before it occurs.

Turning now to the Figures for more system detail, FIG. 1 gives a high-level overview of the system architecture. The device (A) will be a secure container that has digital capability to track the identity and number of articles loaded using a patent-protected coding and marking technology, described in more detail below. In preferred embodiments, the articles are pharmaceuticals. The device would control timing and number dispensed via communication with a networked information system, such as a hospital information technology system (HITS) (B). Through a dedicated application on a mobile device, dispensing form the device may be activated. In certain embodiments, a healthcare worker (HCW) authorized to administer the CS drug (C), initiates the process for dispensing a dose. In other embodiments, proximity to a clinical trials subject activates dispensing, for example, by proximity to a communicating wearable on said subject.

In certain preferred embodiments, CS doses are dispensed in response to an HCW's authorization status that may be confirmed by existing two-factor authentication (e.g., combination of two among biometric, secret password, electronic badge, etc.). The HCW's authorization and the CSDPP's initiation are monitored by the HITS. If the request for dispensing will be in compliance with an authorized CS drug order, the device dispenses a dose (D) the administration of which to the patient (E) will be monitored and confirmed by the HCW. In certain preferred embodiments, CS doses are dispensed in response to an HCW's authorization status that may be confirmed by existing two-factor authentication (e.g., combination of two among biometric, secret password, electronic badge, etc.). The HCW's authorization and the CSDPP's initiation are monitored by the HITS. If the request for dispensing will be in compliance with an authorized CS drug order, the device dispenses a dose (D) the administration of which to the patient (E.) will be monitored and confirmed by the HCW.

In other preferred embodiments, test or control doses are dispensed to a clinical trials subject according to the clinical trials protocol. For example, said subject may be reminded to activate via an electronic device such as a networked mobile phone. The subject's authorization and device initiation are monitored by the clinical trials information system. If the request for dispensing is in compliance with the protocol, the device dispenses a dose (D) the administration of which to the subject (E) will be monitored.

In certain embodiments of the invention, the CDSPP device may be fitted with a disposable cartridge that tracks identity and utilization of individual CS doses carrying a unique identifier (UID). The proper number of doses will be assured by interaction with the HITS and hospital order information. UID data enables tracking utilization, inventory management, and deterrence that will be impossible otherwise.

In certain embodiments of the invention, the UID may be encoded with TraxSecur, a product available and produced by CertiRx in Durham, N.C. Patient privacy may be protected using a TraxSecur UID (TSUID). Moreover, and uniquely enabling for the purposes of this invention, the TraxSecur encoding approach may be more size and shape scalable than other open-format (and hence subject to tampering) machine-readable codes, like barcodes, data matrix, or QR codes. In addition to being applicable at small sizes needed to function directly as a TSUID on individual doses, TraxSecur also can be rendered on screens, paper prescriptions, and most specifically, on the tamper-evident seals described below for sealing CS drug waste disposal cartridges. The TraxSecur code can only be read by our dedicated app, yet only one application will be needed independent of the size or medium on which the code will be rendered.

The CS disposal cartridge also enables rapid deactivation of unused doses wherein their identity and quantity may be efficiently synchronized with pre-existing data records. Moreover, identity of the HCW initiating the deactivation may be tied to the process. Briefly, the cartridge may be fitted to dispose the wasted CS doses inside a disposable bag or other suitable container. The bag may be security-sealed with a UID that links in a parent-child relationship with the number and UID of the wasted CS doses The CSDPP device communicates the disposal event information to the HITS. Disposing the wasted CS doses becomes a secure and a simple process that includes the final check that the deactivated doses have been properly disposed, to include the time and identity of the responsible HCW. Together, these features provide both a strong barrier and a strong deterrent to diversion, as finding misplaced doses will be traceable to particular HCWs in association with specific CSDPP devices and the latter's uniquely identifiable contents. Thus, the CSDPP device of this invention provides a quantitative assurance against opioid waste theft and saves valuable time for auditing substance disposal data.

In preferred embodiments of this invention, the CDSPP device may be designed to deter and detect outright theft of CS drugs through theft of the device (FIG. 1 right side). The CSDPP device is designed to recognize when it has been removed from the network (G.) with which it will be associated in the HITS (F.), i.e., its "home" network. Under such conditions the CSDPP device communicates its location status to its authorized HCW, who may be queried as to whether that location is suspect. If not, for example if it the unit has been transferred to the pharmacy for a refill, the authorized HCW may override CSDPP device's automatic dose inactivation program and notification to law enforcement (H.).

The CDSPP device may be part of an integrated system in some embodiments of this invention, in which case system features can be anticipated in turn to increase patient safety while lowering a hospital's organizational liability and operating costs. It should be expected that with quantitative information about wasted CS doses, physician prescribing practices will be positively impacted. With at least equal importance, the integrated system proposed under this application has appeal to the commercial pharmaceutical manufacturing community. UID-marked CS doses are safer, diversion-deterrent medicines.

What follows are certain details of the integrated system components, structure and process architecture that optimize CS dose and HCW identification, linking both to SOPs, HITS, and CS deactivation/disposal. Together, these features maximize deterrence of CS diversion.

A critical component of the integrated system will be that individual tablets or capsules are labeled with a TSUID. Labeling the CS waste disposal cartridge using the same TraxSecur system creates desirable internal consistencies in system design and operation. The TraxSecur system provides an existing approach to achieving those goals.

TraxSecur may be a data-carrying, optically read authentication mark that securely links physical items to related data tracked by secure digital supply chain management systems. Multi-factor authentication may be a security system that requires more than one method of authentication from independent categories of credentials to verify an identity. On its face, TraxSecur may be a system for detecting and deterring fraud to assure pharmaceutical products in the supply chain. TraxSecur integrates its data-carrying security features with conventional optical or alphanumeric identification codes mandated by governments for track and trace serialization. TraxSecur uses an application on unmodified smartphones to provide efficient multifactor authentication that links pharmaceutical products in the real world with digital tracking in industrial internet of things (IoT) and by blockchain. It does this by measuring changes to text or graphical information inside a border comprised of special symbols (FIG. 2). The symbols also carry a unique serial number that, for additional security, only gets paired with serialization information on the package (and as an outcome of this application, individual doses) at the time a product may be packaged. Finally, and critically importantly from a patient safety perspective, since the TraxSecur mark may be visible but virtually impossible to copy undetectably, it also deters diversion and introduction of unauthorized products to the supply chain in the first place.

When applied to tamper evident labels, TraxSecur can detect changes to text or graphical information inside a border comprised of special symbols. The symbols also carry a unique serial number, like that on a car's license plate. The number may be activated by digitally registering it, making pre-printed TraxSecur labels more secure. A mobile phone application communicates with cloud-base analysis software such that a user receives a simple yes/no response to the authentication or details of suspected changes. Also, since the TraxSecur mark may be overt, it deters diversion.

TraxSecur may be used to secure government-mandated serialization information by enabling mobile phone-based authentication of that information. In all application configurations, however, implanting its high-security features has low barriers. It combines a proprietary symbol set used as a data carrier. The TraxSecur data carrier can stand alone, or it can be used interactively with conventional serialization (alphanumeric serial numbers or machine-readable codes). Whether used alone, as a complement to conventional item-identifying serial information, or interactively with the latter, TraxSecur adds multiple levels for identifying and authenticating products or documents.

Despite its unique and powerful benefits, TraxSecur may be flexible and easy to implement. Any printer or printing technology compatible with TrueType fonts may be a candidate for delivering TraxSecur™ to product, packaging, or documents.

In certain embodiments of this invention, pre-printed labels TraxSecur may be used to uniquely identify the CSDPP device and each CS waste disposal cartridge. These can be applied without risk of theft and misuse through post-application code commissioning. As may be the case with direct print applications, only a mobile phone with camera an application capability may be needed for HCW or law enforcement field identification and authentication of the labeled cartridge, the CSDPP device from which it came, and the identity of individual CS doses the cartridge contains by inference.

In other embodiments of this invention, pre-printed labels TraxSecur may be used to uniquely identify the individual device and each test or control drug cartridge used by a clinical trials subject.

In certain preferred embodiments of this invention, a TraxSecur mark uniquely identifies each individual pharmaceutical dose loaded in a cartridge. FIG. 3 shows that capsules can be labeled with a unique TraxSecur serialized security identifier. The label mark was delivered by a cold laser marking system. The mark may be indelible and does not adversely affect the product. In operation, the TSUIDs may be associated in a parent-child relationship with lot number, expiration date, and any other relevant information as may be required under government mandated serialization. In some embodiments of this invention, the TSUIDs are recorded in a database separate from those that are made public to meet mandated serialization requirements.

In some embodiments, a code rendering may be sent to a mobile device to activate dispensing. Codes would only be sent to authorized persons (e.g., the nurses on duty at the time). Codes would expire according to controlling rules (e.g., could only be used once and not after a set time). This feature has additional benefits once the patient takes a device home, as it monitors compliance with release order and number of doses taken, data from which could positively affect physician prescribing practices. In preferred embodiments, the code sent to the mobile device may be a TraxSecur code.

As explained in more detail above, the cartridge may include a tamper-evident seal (FIG. 4). With respect to doses that have not been dispensed, uniquely identifiable doses remain in the container, thus deterring their diversion prior to destruction (in the case of CS doses) or enable accounting for unused doses (as is useful in clinical trials, for example).

In some embodiments, the device would send an alarm if removed from its home network without permission, allowing law enforcement to be engaged and track down the device once it may be established that a theft has occurred. Law enforcement could be provided with the identity of doses remaining in the device should they become separated.

Figure 6:
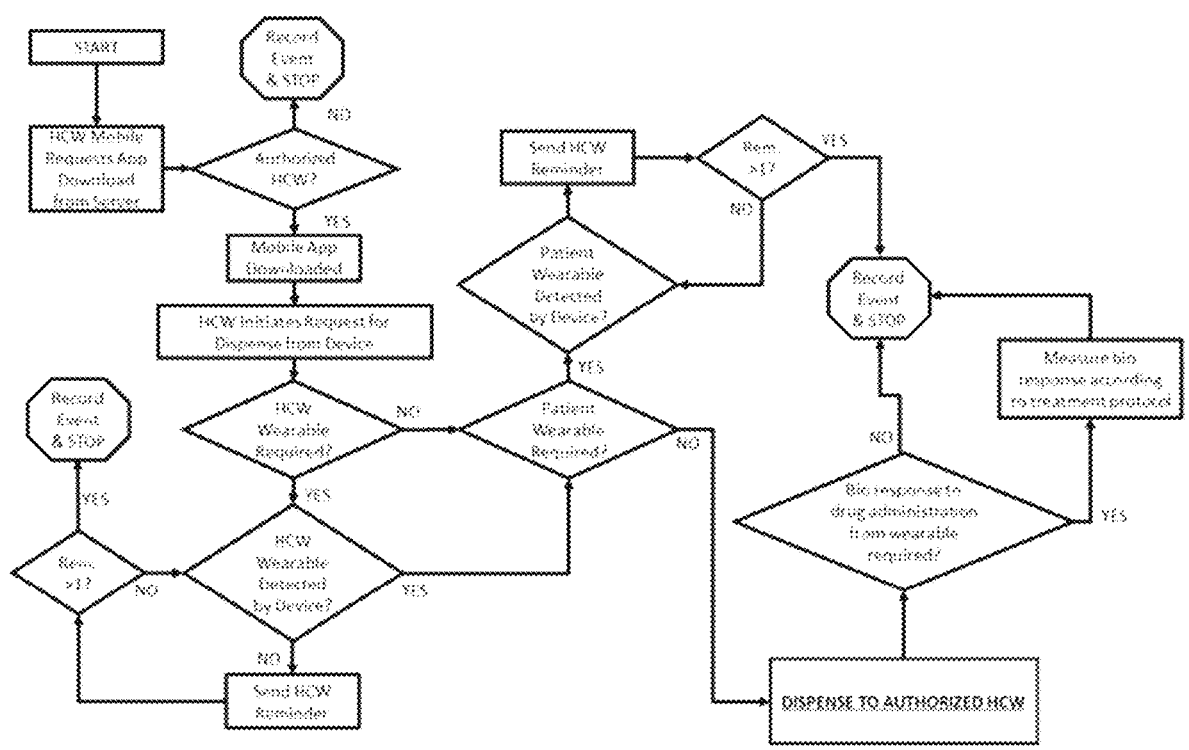

A flow chart detailing the logic behind preparing the CSDPP device for use may be given in FIG. 6. The tamper seal bearing a TSUID may be affixed as a label the CS waste disposal bag. Then the device may be filled with CS drug doses and the disposables that constitute the CS waste disposal cartridge. Alternatively, the cartridge may be pre-filled with doses prior to loading, in which case steps called out individually in the flow chart may be delivered "pre-packaged" as part of a ready-to-load, cartridge. The cartridge may be a blister pack. Labeling doses may occur before or after inserting doses in the blister pack.

In any case, the TSUIDs corresponding to the pharmaceutical doses may be read and stored in the device memory. During the reading step, if any TSUIDs reads are either replicates of authorized but previously used TSUIDs or TSUIDs that have never been commissioned for authorized use, the device will flag that there may be diverted material or (more likely) fraudulently misused information. The device also assures that the dose number may be consistent with the hospital order or clinical trial protocol, as appropriate. Once all internal checks are consistent, the TSUID of the tamper label may be associated with the loaded doses in device memory, making the device ready for deployment to dispense.

FIG. 6 gives the logical flow for operation of a CSDPP device once it may be filled and deployed for dispensing. The first steps show control on application download to associate an HCW user with a 2-factor authentication login, which should always include a biometric, like a fingerprint reader or face recognition. Next, the application on an authorized HCW's application may be synced with a patient's hospital order for the CS drug. An authorized HCW enabled to dispense the CS drug, but system logic assures that dispensing may be always in compliance with the hospital order. Similarly, embedded rules may control when a refill request gets sent to the pharmacy.

The CSDPP device may be also enabled to deter and detect theft, as also shown in FIG. 6. The device monitors its own location and its connectivity to an expected home network. If connectivity may be lost with the home network, the device alerts the authorized HCW and HITS. The HCW applies human intelligence to an assessment of the likelihood a theft has occurred, versus other causes like a network failure. In cases where theft may be expected, the HCW may allow law enforcement to be engaged and track down the device. If engaged, embedded rules would allow law enforcement to be provided with the device unique identity, unique identity of the disposal cartridge, and most importantly, TSUIDs of doses remaining in the device should they become separated. Note that no patient information need be transmitted to facilitate arrest and prosecution of stolen doses.

Together, the features and process of the system, device, and compositions of this invention provide a compelling deterrent to diversion or theft of CS doses to the HCW and all who come in contact with the CSDPP device.

Moreover, CSDPP system design may integrate with the deterrence and diversion control aspects of the Drug Supply Chain Security Act (DSCSA), enacted Nov. 26, 2013. DSCA outlines requirements to build electronic systems that identify and trace, at the package level, prescription drugs distributed in the US. According to FDA, implementation of DSCSA creates a tighter, closed distribution system for prescription drugs to prevent harmful drugs from entering the supply chain, detect harmful drugs if they do enter the supply chain, and enable rapid response when such drugs are found. As the CSDPP device system will link individual doses to package-level serialization, we will leverage and extend the benefits of DSCSA to deterring and detecting CS drug diversion.

In preferred embodiments, the system integrates into the pharmacy dispensing systems currently in place in many hospitals. After an order is entered into the electronic health record (EHR) ordering system by the provider HCW, it is typical that another HCW closer to the patient bedside will receive pharmacy verification then will withdraw the medication from a secured, automated dispensing cabinet. The CS drug may be administered at the bedside with scanning of the local HCW's badge, the barcode on the patient armband, and the barcode on the CS drug packaging. Specific Aim 1. Develop a TSUID reading and recording mechanism that may be consistent with incorporation into a room-size device capable of delivering CS doses on demand under control of an authorized HCW.

In certain embodiments, the CSDPP device will be restricted to dispensing capsules, solid oral dosage forms, or pre-filled syringes. In preferred embodiments, the CDSPP device may dispense more than one of said dosage forms.

Independent of dosage form, each dose may have a unique TSUID data carrier. For example, the dosage forms may be marked with a cold laser of the type available. This marking method utilizes the common brightening agent $TiO_2$. Direct exposure of such capsules to a beam from a UV laser permanently converts $TiO_2$ to a new crystal structure, with a color change from white to blue/gray. This labeling process causes neither the structural weakening or unwanted by-products of burning associated with laser engraving process and has higher resolution than any ink-printed mark.

In preferred embodiments of this invention, the CSDPP device is equipped with a dedicated camera system to read doses bearing TSUIDs and locally record that information. The camera configuration is suitable for use within the general design framework of a CSDPP device that dispenses doses. The camera system may be incorporated into a modular design consisting of three parts: communications, control, and power modules.

Example 1—TSUID Reader/Dispenser Module

Illustrated in FIG. 5, the Left Panel illustrates one embodiment that is tested in this example. Component (A) is a dose moved by a translation mechanism, (B), into a reading window or location, (C). The dose is marked with a UID, which is shown in this case as a TSUID. A rotating mechanism, (D), assures that the UID is visible to an imaging device, (E) In the Right Panel, Components (A) through (C) are substantially equivalent functionally to those of the previously described embodiment. In this preferred embodiment, multiple imaging devices viewing substantially the entire dose surface (shown here as cameras labeled E through G) replace the rotational mechanism.

It is clear to the skilled artisan that the dose represented herein as a capsule may be a solid oral dosage form, a prefilled syringe, or any of a variety of item shapes or sizes. Moreover, said artisan understands that the mechanisms imaging devices described may be in a variety of functional forms.

Turning now to the steps of this Example 1:
a) Capsules (empty, white, size 000) are labeled with 100 different TSUIDs, each in replicates of three, at each of 4 mm, 3 mm, and 2 mm square. On one set of capsules, TSUIDs will be delivered at 120 degrees around the capsule body; on a second set, TSUIDs are positioned on the top or bottom of the capsule shell.
b) For simpler, more reliable, and more cost effective (compared to rotating a dose into a reading view): i. TSUID is read from one of several positions on a capsule; and ii. read from a single TSUID position from multiple camera views.
c) TraxSecur software performs an image correction from curved surfaces to allow comparative sensitivity, reproducibility, and speed of reading TSUIDs in multi-camera configuration versus the single camera configuration. The outputs recorded include the following: quantitative read rate for TSUID (i.e., required dwell time vs. read failure rate, etc.) Likewise, the effect of label size and radius of curvature is determined, as these are critical parameters for labeling small individual doses and translate to our ability to label solid oral dosage forms and pre-filled syringes.
c) The CSDPP device's dose dispensing capability with image capture TSUID reading, recording, and ESD is demonstrated, including its compatibility with full 4G and 5G interconnectivity, GPS location, and simulated voice command interaction with authorized HCW's.

Compatibility of reader/dispenser module is shown with a covert option that will capture specifics of the surrounding environment and tied to ESD, e.g., image capture of room and HCW. Output is testing of camera, dispensing, notification and communication functions.

d) Parent-child relationship is demonstrated between TSUIDs and simulated data required for serialization compliant with government mandates. A TSUID is attached to each module using appropriate implementation mode, i.e., tamper-evident seals on hardware components, cold-laser marking on doses. TSUIDs are locked synchronously at the point of a CSDPP device's commissioning, simulating the hospital dispensary or approved packaging facility. Performance of multiple units is simulated by resetting a CSDPP prototype to three sets of models UIDs. The three model UIDs become one with the parent CSDPP device "unit" and are linked to a prototype CSDPP device cloud-based database. CS dose TSUIDS are linked to a simulated electronic batch records (EBR) via a database exchange and interface without linking patient-identifying information. A blockchain having private nodes is an example of such a database exchange. Outputs are validated relationship between the parent-child relationship of the TSUID and simulated data.

Example 2—CSDPP Device

A flow chart detailing the logic behind a CSDPP device of this Example 2 is given in FIG. 6. A healthcare worker (HCW) requests download of a mobile application that controls CS drug dispensing from a device or deactivation of unused doses in the device. If the HCW is authorized to use the app, download proceeds. Optionally, the authorization comprises linked authorizations of a device assigned to a patient or patients. In this Example 1, the HCW is required to have a wearable paired to the device, such that dispensing may only be activated within a specified proximity between the wearable and the device. Presence of the HCW's wearable is confirmed. Likewise, in this Example 1 the patient is required to have a wearable paired to the device, such that dispensing may only be activated within a specified proximity between the wearable and the device. Presence of the patient's wearable is confirmed.

Once HCW wearable, patient wearable, and device are detected all within the specified proximity, the HITS checks to assure that the request for dispensing is in compliance with an authorized CS drug order. That compliance is confirmed, and the device dispenses a dose, the administration of which to the patient is monitored by video recording and confirmed by the HCW.

The wearable on each of the patient and HCW measure biological responses after the dose has been administered. The patient's heart rate and respiration are depressed after about 20 post-CS drug administration. The patient's heart rate and respiration are depressed after about 20 post-CS drug administration. The HCW's heart rate and respiration are unchanged immediately after CS drug administration. Together, these results confirm administration of CS drug as directed, without a diversion event likely.

Data from the preceding events are tracked on a blockchain system. The CSDPP device is a private node on the chain, assuring that no access to patient or HCW identifiable information is accessible to unauthorized parties.

Turning now to FIG. 7 and events in this Example 2 relating to an HCW's instruction to dispose of unused doses in the CDSPP. FIG. 7 shows the configuration of a special purpose blister pack from which CS drugs, formulated as capsules in this Example 1, have been dispensed and remaining doses are deactivated. The skilled artisan recognizes that it is possible to configure similar dispensing from a conventional blister pack.

A parent security-label identifies the individual dose UIDs comprising the load on the illustrated pack. Components of the special purpose blister pack are shown in FIG. 7 from top and side views as follows:
A. Blister foil
B. Blister
C. CS capsule doses
D. Liquid communication channels
E. Deactivation solution injector needle
F. Deactivation solution
G. Pressure relief needle The CDSPP device receives a deactivation command from the authorized HCW, the deactivation solution injector needle and pressure relief need pierce dedicated empty blisters. The deactivation solution is injected and flows through all chambers of the blister until detected at the pressure relief needle. The deactivation solution contains an antagonist to the CS drug. The skilled artisan recognizes that the deactivation solution may be any material that makes the doses inaccessible or ineffective.

Example 3—Clinical Trials Subject Compliance Device

Figure 8:
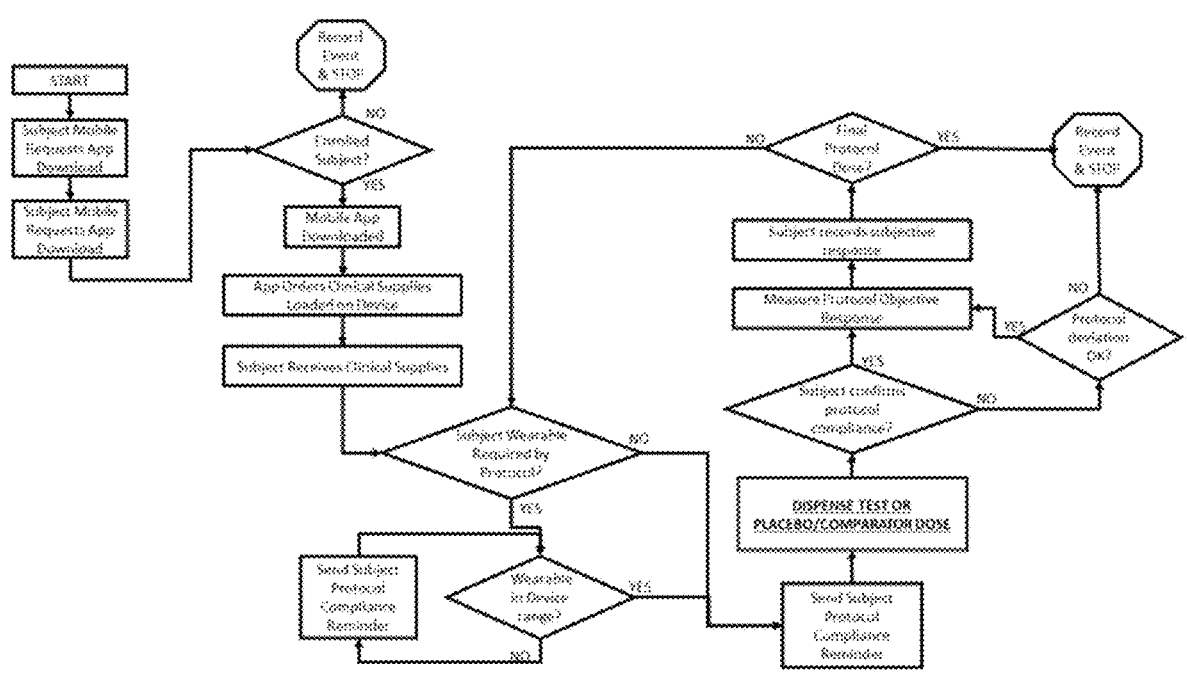

A flow chart detailing the logic behind a device useful for monitoring clinical trials subjects' protocol compliance this Example 3 is given in FIG. 8. Blinded administration of any combination of test drug or comparator control drug or placebo is a special feature of illustrated in this example. However, the skilled practitioner recognizes that this feature is not required for the device to be useful in monitoring subjects' protocol compliance.

The clinical trials subject compliance device has been delivered to the subject, each loaded with blister packs that house either test drug or control drug or placebo doses. The skilled practitioner recognizes that a single blister pack that house some combination of test drug or control drug or placebo is an alternative and may be a more effective option where random administration between two or among three is desirable in the trial design. In this Example 3, the test drug is a new non-narcotic analgesic, control drug is oxycodone as a comparator, and placebo doses have no active ingredient. All three are formulated to look identical, but each type is labeled with UIDs assigned to one but not the other two groups. Subjects are recruited for a trial to commence immediately after a routine molar extraction procedure.

Prior to commencement, the trial subject requests download of a mobile application that controls test, control, or placebo dispensing from the device or deactivation of unused doses in the device. If the subject is authorized to use the app, download proceeds. In this Example 2, the subject is required to have a wearable paired to the device, such that dispensing may only be activated within a specified proximity between the wearable and the device. Presence of the subject's wearable is confirmed.

Once the subject's wearable, and device are detected all within the specified proximity, a network call is made to the clinical data management system (CDMS), which then checks to assure that the request for dispensing is in compliance with the trial protocol and selects among drugs onboard the device accordingly. The device dispenses a dose, the administration of which to the patient is monitored by video recording and confirmed by the subject.

The wearable on the patient and subject measures biological responses after the dose has been administered. The patient's heart rate and respiration are depressed after about 20 minutes post-control administration, but not for test or placebo administration. The patient's reports pain level blinded to whether test, control, or placebo has been administered.

Data from the preceding events are tracked with the CDMS. After unblinding, the correlated subjective pain data are available and provide a direct comparison of test drug vs comparator control drug vs placebo, all measured in individual subjects.

It is a regulatory requirement to have audited collection of unused clinical supplies in this trial. It is desirable that unused narcotics be deactivated to avoid non-compliance with audited collection. Turning to FIG. 9, dispense and deactivation components of this Example 3 are shown from top and side views as follows:
  A. Deactivation solution injector needle
  B. Needle channel
  C. Dispense plunger
  D. Blister
  E. Blister foil
  F. UID-labelled tablet dose
  G. Deactivation solution The left panel shows components' initial position in the device. Dispensing is affected by the plunger pushing the dose through the blister foil, as shown in the center panel. Note that the deactivation needle remains in its initial position, but the skilled artisan recognizes that the needle may move in concert with the plunger without piercing the blister or contacting the dose.

The CDMS sends a signal to the device to deactivate doses that will not be used in the trial. An inventory of remaining UIDs is collected by the device. The deactivation needles then pierce the blisters and deactivation solution (described in more detail in Example 2.) is introduced. The device and deactivated doses are returned to the trial sponsor.

Example 4—CS Waste Dose Disposal Module that Holds Doses for Dispensing

Figure 10:
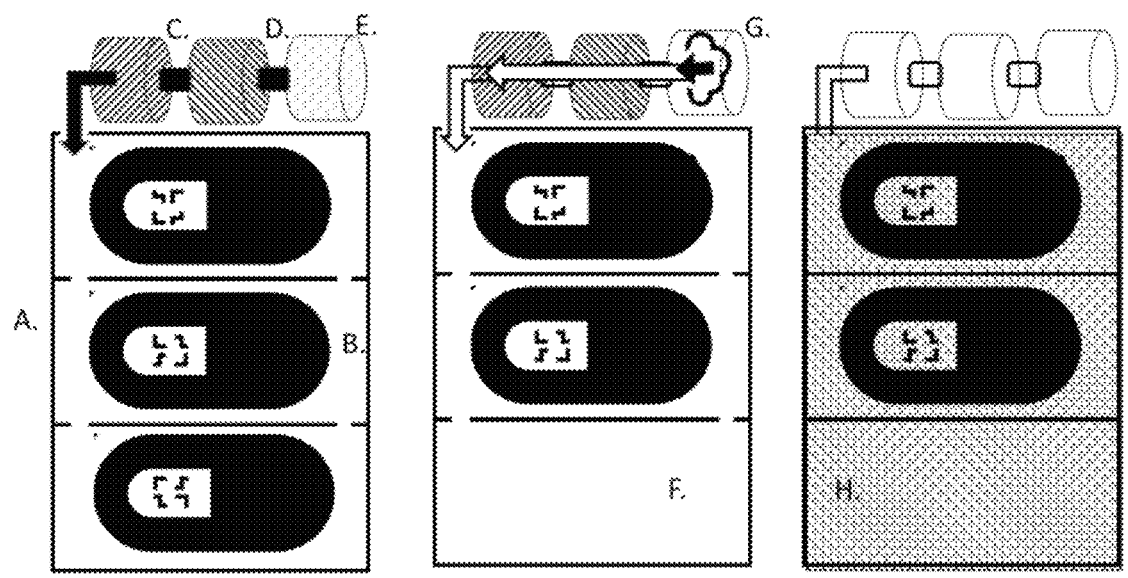
Figure 11:
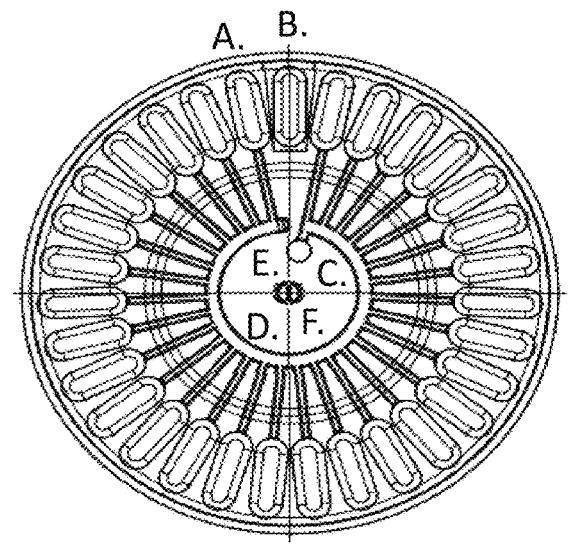
Figure 11:
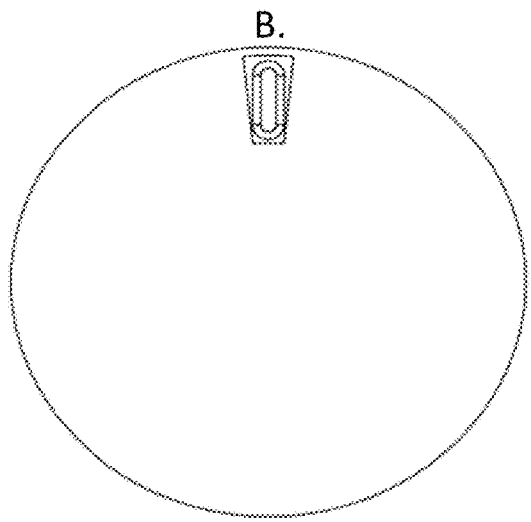
Figure 11:
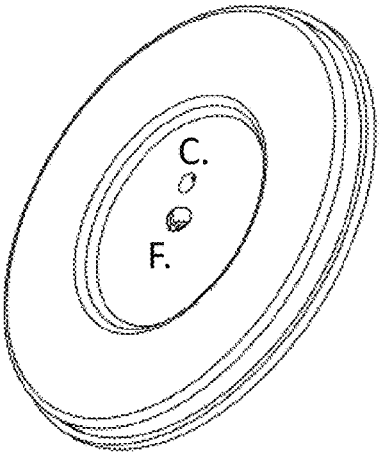
Figure 11:

FIG. 10 illustrates a representative cartridge for holding doses to be dispensed, said cartridge further comprising a mechanism for deactivating doses. In the example shown here, the Left Panel shows a holder component, A, in which doses, B, are held pending dispensing. The dispensing mechanism may be shared with the translational or rotational mechanisms of the previous example or may be separate mechanisms. The holder may allow for liquid communication between segments. The holder also is associated with a deactivating mechanism. The deactivating mechanism shown here is two liquid components (C and D) that may be components of a fast setting epoxy. The Left Panel also shows a charge, (E). The charge is a nail gun cap, a $CO_2$ cartridge, a spring-loaded mechanism, or any other charge capable of activating the deactivation mechanism. The Center Panel shows one of three doses having been dispensed from the cartridge from a representative location (F). The Center Panel also shows the approximate instant of charge activation (G) and approximately concomitant opening of barriers between epoxy components and between those components and the cartridge holder space. The hatched area (H) in the Right Panel represents hardened epoxy in which doses that remained in the holder are embedded and thereby inactivated The skilled artisan would appreciate that the dose represented here as a capsule may be a solid oral dosage form, a prefilled syringe, or any of a variety of item shapes or sizes. Moreover, said artisan understands that the holder may be configured differently for each shape or size held, and that the deactivating mechanism may be integral to each cartridge or a separate component. Those skilled in the art of this invention also appreciate that the epoxy is merely exemplary, and that deactivation may be affected with a variety of alternative approaches, including without limitation, introduction of: i. pharmacologic neutralizing agent, like the opioid antagonist naloxone; ii. a solvent for the doses; iii. mechanical deactivation, for example, by crushing; iv. combinations of the foregoing.

Turning now to the steps of this Example 4:
  a) Three different cartridge configurations are designed and built using 3D printing technology wherein each can bear a parent TSUID as a tamper seal and can be pre-loaded with CS doses or manually loaded by a user, each labeled with a TSUID. All three cartridge configurations are designed to fit in a single CSDPP device dose delivery mechanism. Tested and validated is the reliability of TSUID read upon dispense instruction receipt by the device/cartridge combination and reliability of actual dispense (time to delivery, subjective dose condition assessment, etc.) for each configuration, each across a minimum of 100 dispense instructions sent to the cartridge loaded on a prototype CSDPP device mechanism.
  b) A CS waste disposal cartridge that can hold doses for on demand dispensing is primed for rapid deactivation of those doses upon instruction from an authorized HCW or autonomously under circumstances where it is highly likely that the CSDPP device has been stolen is designed and built. The CSDPP device keeps an inventory of the CS doses that the CS waste disposal cartridge contains. In one alternative design, loading the CSDPP device for deployment to a patient is simulated as if done by a local the attending pharmacist. In another alternative design, the cartridge that has a parent TSUID as a tamper seal that will link to pre-loaded CS doses, each labeled with a TSUID. A protocol is coded in the device logic to protect the payload from accidental deactivation (e.g., by authorized HCW override), and protects the patient's identity while capturing environmental information that can be provided indirectly or directly to law enforcement once a simulated hostile attack is detected. Accordingly, the device has three levels of home base "heartbeat" interaction with set protocols linked to trigger, in order, input from the particular device's simulated authorized HCW and HITS, followed by automatically engaged protocols in cases of i. deactivation instructions from said HCW or HITS; simulates engaging law enforcement ii. upon authorized user instructions or iii. if communications are lost.
  b) A control system is designed which optionally may have components selected from the list: a gyroscope, accelerometer, and an impact detection sensor, all to be used to detect if there is an attempt to access the contents without authorization and control. These sensors are implemented to be configurable to prevent false alarms in cases of intended movement of the CSDPP device, such as in future versions used in the home or elder care setting. The sensors are set to detect the human interaction measured in conjunction with 20 naïve users instructed to "steal" or "break into" the prototype versus 20 simulated events where naïve users are told to "move the unit across the room" and programmed to avoid alarms from the latter set or upon instruction from a simulated authorized HCW c) A stored energy charge that will deactivate CS doses if triggered by encapsulating the cartridge payload contents in quick hardening epoxy is incorporated in the cartridge design. The charge is selected from among the list: a $CO_2$ cartridge; a stapler cap, or spring-loading mechanism. In one alternative design, the charge is integral with the cartridge. In another alternative design, the cartridge and charge are separate to allow the charge to be reused in cases where an empty cartridge is disposed without activating the encapsulating material.

d) Based upon the best-performing design from a)-c), above, a design is finalized. Deactivate CS doses is tested after triggering encapsulation by the cartridge contents in quick hardening epoxy. Time is measured to hardening from deactivation instruction and shown to be less than one to 10 minutes. Deactivation is demonstrated by subjectively assessing failure of 20 naïve users that were instructed to "remove CS doses" from hardened epoxy.

Example 5—Rotary Cartridge Dispense/Deactivation System for Outpatient Delivery of MAT This Example 5 illustrates a dispensing and deactivation system, method and device for MAT delivery in an outpatient setting such that certain aspects of a "qualified practice setting" are achieved. This system, method and device combines dose dispense and deactivation functionality inside of a disposable rotary cartridge. FIG. 11 illustrates a view of multiple orientations of the rotary cartridge with the top left panel providing an aerial view. Component (A) shows a ring of compartmentalized dose housings oriented around the perimeter of the top component of the cartridge. Component (B) is an opening in the bottom component of the cartridge through which doses exit during a dispense event. Component (C) shows the fixture point of a resin reservoir which flows into a (D) channel of veins that lead to the dose housings during a deactivation event. The resin is blocked from flowing through the dispense hole and previously dispensed dose housings by component (E) Component (F) is a clip that connects the top and bottom components of the cartridge. The top right panel shows the bottom side of the cartridge providing an improved view of the (B) dispense hole. The bottom left panel uses an opaque material for the top component of the cartridge to highlight (C) the connection point between the resin reservoir and (F) clip used to hold the top and bottom together. The bottom right panel shows the slim form factor of the rotary cartridge.

FIG. 12 shows a high-level system illustration of the dispense-deactivation component of the system, method and device. Component (A.) shows the side profile of the rotary cartridge, controlled by a (B) stepper motor that is triggered to turn in discrete increments. A (C) viable camera, in this case illustrated as a mobile phone component with TraxSecur scanning software onboard, is mounted to scan dose TSUIDs as they travel through the cartridge. A dispense event will not occur until the TSUID of the dose has been verified.

In the event of an attempted intrusion or if an unregistered dose is detected, a (D) spring-loaded plunger is released to displace resin from its (E) reservoir and into the rotary cartridge. When the resin has fully encased the doses in the rotary cartridge, (F) UV LED arrays are activated to cure the resin. The hardened material surrounding the dose will act as a temporary deterrent for an unauthorized attempt to remove the doses from the cartridge. Other logical rules that may cause activation of the plunger as described include, without limitation, expiry of a prescription, removal of the device from its home network, e.g., in case of attempted theft.

The rotary cartridge is a disposable, injection molded part designed to be discarded each time a new prescription is filled. A drug manufacturer fills the cartridge by placing the doses on the bottom component of the cartridge and clipping the top component in when fully loaded. An alternative approach is to load the doses into the dispense port while simultaneously rotating the cartridge. Alternatively, empty cartridge components may be supplied to a dispensing pharmacist for filling as described above. An automated system for dose population increases speed and control in each of the above scenarios. A transparent material is selected for the top component of the cartridge to allow for high UV light transmission and for reading TSUID information from the doses.

A concentric ring design is implemented to increase capacity for MAT CS doses. Optionally, this design accommodates different types of doses for users with multiple prescriptions. The bottom component of the cartridge has a dispense port for each ring, each in combination with a series of stepper motors for individual ring control. An alternative method of rotation is to use a compressed spring that is partially released during a dispense event. Optionally, a linear cartridge is utilized when a longer and skinnier form factor is desirable. A linear design uses guides to move the cartridges over a dispense port.

Enabled by the material selection of the cartridge, the UV laser marking system is used to label doses with TSUIDs on pre-filled cartridges. This approach simplifies the process of orientating doses inside of the device and eliminates using a camera sensor array with 360-degree coverage. A low coefficient of friction causes the dose to roll when a rotation event occurs. Therefore, all surfaces of the dose is exposed to the camera. A mobile phone with TraxSecur software is mounted above the cartridge to scan dose TSUIDs before they are dispensed. In the event of an unregistered TSUID, a deactivation event will occur. Alternatively, doses pre-labelled with TSUIDs are used to fill the cartridge, in which case it is preferable to verify the TSUIDs prior to any dose dispense event.

The mechanism for deactivation utilizes a potential energy to kinetic energy conversion through the release of a compressed spring. A flat disk is attached to the spring to provide an equal force over the top layer of a resin reservoir. Resin is shunted through a port in the bottom of the reservoir and flows into the cartridge. An alternative approach uses an electronically controlled pump which would allow for higher volume control but slower travel time and higher power draw.

UV curing, a photochemical process that uses ultraviolet light to cure resins comprising of photoinitiator molecules, is used in this system, method and device for deactivating MAT doses. Photoinitiator molecules are activated by high intensity UV light causing polymerization of the resin and a transition from liquid to solid form. Two high intensity LED arrays are mounted above the cartridge to provide full light coverage. The LEDs are powered on after a programmed time period to harden the resin. A biocompatible resin is used as a safety against attempts to ingest the doses after being embedded in resin. Optionally, an opioid antagonist, like naloxone, is incorporated in the resin as an additional safety measure.

In certain embodiments, it is desirable that the resin for deactivation or any other liquid deactivation solution like an opioid antagonist be delivered only to cartridge positions that still contain an article, and not to any spent cartridge position. FIG. 13 shows a rotary cartridge design for achieving this desired effect. In the top left panel, the cartridge is shown from the deactivation solution injection side plate. The deactivation liquid is injected into a distribution reservoir (A) that has holes (B) that channel to each cartridge article location. The cartridge is shown from the dispensing side in the top right panel of FIG. 13. The dispensing side comprises another plate that rotates independently of the injection side plate. Note that the dispense port (C) is not aligned with the reverse side of holes (B) descending from the injection side, but each article location in the cartridge (D) is initially aligned with a hole and connected thereto by a joining "journal" channel (E) that also is a feature of the injection side plate. In the bottom left panel of FIG. 13, rotation of the cartridge to put the first article (F) in the dispense port, and that by doing so slides dispense side plate such that the journal is no longer aligned with the corresponding hole. Other article location holes and journals remain aligned. The lower right panel shows that the spacing of holes and journals put holes and journals out of alignment for empty, but not filled cartridge positions.

Example 6—Rotary Carousel for Remotely Monitoring and Controlling Methadone Take-Home MAT This Example 6 illustrates a dispensing system, method and device for remotely supervising methadone dispensed for take-home MAT. This system, method and device combines dose dispense and deactivation functionality inside of a locking box or travel case that houses a carousel. The carousel and associated mechanical and electronic components monitor and control liquid methadone doses housed in individual vials.

Turning now to FIG. 14 illustrating a representative dispenser component of the system of this Example 6, an exploded view is shown in the left panel and a front view of a partially assembled unit in the right panel. A locking travel case (A) houses mechanical and electronic components. Mounted on base plate (B) are a power source (i.e., batteries, a power supply, or in preferred embodiments, a power supply with battery backup), electronics for mechanical control and communications electronics. Stand offs (C) create space above the base plate for a motor (D), locking solenoids (E), and a carousel (F) for holding vials (G). The carousel has notches or holes into which the solenoid plungers extend to prevent rotation. A top plate (H) is affixed above the preceding components and seals off access to all but one carousel position. The top plate has a button for user control and a display for external communication and device status information.

FIG. 15 shows an alternative embodiment for the electromechanical components of the device of this Example 6. As above a baseplate (A) and stand-offs (B) are used. A spindle with drive gear and position sensor (C) is linked to motor (D), such that the gear ratio is high enough to prevent turning the spindle. A worm gear drive is an example of drive gearing with such a ratio. The spindle runs through a mid plate (E) to control rotation of a substantially flat carousel (F) intended to hold vials. Rotation of the carousel slides vials around on the mid plate. In certain embodiments, a secondary plate may be preferred to rotate in unison below the carousel plate, serving in part as a frictionless support for the vials. As described above, a top plate is a mounting location for user controls, like a button, a communications display, and seals access to all but one carousel position In preferred embodiments, the communications capabilities of devices of this Example 6 comprise mobile networks, Bluetooth, and WiFi. Likewise, devices are comprised of sensors for location (i.e., GPS), temperature, humidity, vibration, shock, and light intrusion.

Vials are filled at an outpatient treatment program (OTP) according to a patient's order. Each vial bears a unique identifier, which may be limited to the patient identifier, date, dose, and sequence number among the total number of vials ordered or may us some other unique identifier, like a TSUID, a bar code, data matrix, or radio frequency identifier (RFID). The device is loaded by qualified OTP staff with the identity of each dose by position tracked in a database and displayed on a dashboard, like the one illustrated in FIG. 16. The dashboard is comprised of certain summary information about the patient (A), the associated device identifying information, and visual inventory of vials (B).

Status of the vials is remotely monitored and controlled, again with visualization on the dashboard. Location of the device may be displayed (C) along with detailed event logs. In certain preferred embodiments, removal and return of a vial is detected via optical, electronic, or physical sensors. In such embodiments, the sensors also may detect if a vial is full, empty, or partially full, for example, by monitoring the vial weight. The upper panel of FIG. 16 shows remote monitoring of the patient removing a vial. In the lower panel, the empty vial has been returned to the device, inventoried, and the next dose rotated for dispensing.

In preferred embodiments, the dispensing from the device may be deactivated remotely from the dashboard (D) or autonomously when sensor thresholds are exceeded, device location is out of preset bounds, or with a machine learning algorithm that predicts patient distress or device theft. A device with dispense so deactivated may be unlocked remotely by the OTP from the dashboard control.

In certain embodiments, it also may be desirable to have deactivation with a hardening resin (as described above in example 5). FIG. 17 illustrates a system for incorporating said deactivation with the device of this Example 6. A UV transparent lid with reservoir (A) has liquid communication via journals (B) to vial cap or lid locations (C). In preferred embodiments, photocuring hardens the lids to the vial and carousel (D), making removal of the vial difficult. The skilled artisan recognizes that the lid illustrated in FIG. 17 is equally adaptable to the substantially flat plate carousel illustrated in the device of FIG. 15.

The skilled artisan recognizes that the carousel exemplified in the systems, methods and devices of either Example 5 or Example 6 has as one of its functions to move vials from inaccessible locations to an access point or points. In alternative embodiments said function may be achieved with a conveyer belt. The conveyer belt may be linear or serpentine. In other embodiments, the vials may remain stationary while the access point is moved to make one or more of the vials accessible. For example, the carousel of Example 6 may be held fixed while a round insert in the top plate is rotated to move the access point.

The skilled artisan also recognizes that the access point may be open as illustrated in the devices of Example 5 and Example 6 and in alternative embodiments may have a secondary barrier like a door. The door may have a secondary locking mechanism.

The skilled artisan further recognizes that vials illustrated in the devices of Example 5 and Example 6 may alternative embodiments be uncapped or may be replaced by removable cups in the carousel or belt.

The skilled artisan recognizes that the systems, methods and devices of the present invention may further comprise network links, human interfaces, and communications capability such that certain aspects of a "qualified practice setting" are achieved. These systems, methods and devices including those of either Example 5 or Example 6 further may comprise biometric login by fingerprint reading and patient identification. Optionally, iris scan or facial recognition is used in addition to or instead of the fingerprint reader, in which cases the biometric read also provides information about patient condition to the practitioner, e.g., motion tracking or pupillary dilation tests. These systems, methods and devices further comprise a touch screen or linked mobile device with telemedicine functionality, thus giving the patient ready access to her/his practitioner(s). DOXY.ME is an example of said telemedicine function. These systems, methods and devices still further comprise data communications capability that fills medical record information about, without limitation, device GPS location, patient status (including physiological biometrics recorded from patient wearables or interactions as described above), and timing of requested and dispensed doses. These systems, methods and devices also comprise emergency first-responder call functionality when a crisis is detected with respect to patient or device status.

The compositions of the present invention are machine verifiable marks comprising embedded unique identifiers on pharmaceutical, nutraceutical or recreational drug dosage forms or other articles, wherein said marks are a component of a system for tracking, dispensing or deactivating related articles.

The compositions of the machine verifiable marks of the present invention includes those with one or more reference characters. The reference characters may be alphanumeric characters. In preferred embodiments of the present invention, the reference characters are reference characters functional in the "gridding" method described in U.S. Pat. No. 9,053,364.

In compositions of the machine verifiable marks of the present invention, one or more reference characters are provided on a predetermined arrangement map, as is illustrated in FIG. 2.

The one or more reference characters may be placed onto the image in a random position and at a fixed frequency, wherein the frequency array of reference character ("entity") by type ("cluster") comprises at least two distinct clusters of entities having detectable counts or relative counts per cluster ("signature array") that encodes a product authentication code as is more fully described in U.S. Pat. No. 7,874,489.

The one or more reference characters may be placed onto the image in a random position and at a random frequency. The authentication identifier may define orientation marks. Comparing the predetermined arrangement map includes comparing the orientation marks of the authentication identifier with orientation marks of the true authentication identifier.

Compositions of the machine verifiable marks of the present invention include those wherein one or more reference characters are provided on a predetermined association or correlation with numeric values, as is in FIG. 2. The skilled practitioner recognizes that the particular set of associations and correlations illustrated is just one of many such sets. Larger sets may be associated with alphanumeric characters such that each association or correlation carries more than a single digit of information. For example, the "L" character might be associated with "3" as shown of "a", "#", etc., and thus be associated with "23", or "4000", or any one of an infinite number of possible numeric value The skilled practitioner also recognizes that the systems, devices, and compositions of this invention may be usefully integrated with the deterrence and diversion control aspects of the DSCSA, including without limitation, its electronic systems that identify and trace, at the package level, prescription drugs distributed in the US. The skilled practitioner further recognizes that the compositions of this invention may be usefully integrated with other electronic data systems, like blockchain.

The skilled practitioner recognizes that the systems, devices and compositions of this invention may be clinical trials users, in which applications these are useful in assuring subject compliance to protocols, clinical supplies management, and returns, the latter in particular where CS medications are part of the trial. Moreover, it is apparent to the skilled practitioner that the examples given are illustrative of the compositions disclosed herein and are not meant to be limiting.

Certain preferred embodiments of the present inventions may include a computing device comprising: a processor and a memory operable to: capture an image of machine verifiable marks comprising embedded unique identifiers and error correction features borne by a candidate article subject to identification or authentication; extract a unique identifier from the corrected mark; and determine, based upon a comparison between the extracted unique identifier and match information, whether the candidate article is a reference article. In such embodiments, a relationship between the unique identifier and identification or authentication is stored in a database. A blockchain having private nodes is an example of a suitable database.

What is claimed:

1. A device comprising:
    a cartridge for holding vials to be dispensed, wherein each vial contains an article and wherein each vial is separated one from another in respective discrete cartridge locations within the cartridge such that a selected one of the vials may be selected for being dispensed;
    processor-executable instructions that can cause a computer to select among the discrete cartridge locations containing a vial to be dispensed by the dispenser,
    a dispenser for dispensing the vials from the cartridge, wherein the dispenser is directed to which of a selected cartridge location contains the selected vial, and the dispenser dispenses the vial from the selected cartridge location;
    a deactivation assembly configured to deactivate the vials remaining in the cartridge with a hardening material that comes in contact with the vial but not directly with the article due to the article being contained within the vial.

2. The device of claim 1, further comprising a memory capable of storing inventory information about the articles, wherein the inventory information is the number of articles loaded, dispensed, and remaining in the device and wherein the inventory information further comprises unique identifier information about the articles.

3. The device of claim 1, wherein the deactivation assembly comprises a stored energy charge.

4. The device of claim 1, wherein the deactivation assembly for deactivating is triggered in response to environmental sensors.

5. The device of claim 1, wherein the articles are pharmaceuticals, nutraceuticals or recreational drugs.

6. The device of claim 1, wherein the processor-executable instructions comprise a signal received from a source selected from among the group: a motion sensor, an acceleration sensor, an impact sensor, a gyroscope, a user wearable, a GPS location, an onboard mobile network connection, a paired mobile device, an internet connection, a Bluetooth connection, an elapsed time measurement, or sensors that monitor removal and return of a vial.

7. The device of claim 1, wherein the cartridge is a rotary cartridge.

8. The device of claim 2, wherein the inventory information is tracked in an external database.

9. The device of claim 1, wherein instruction information is tracked in an external database.

10. The device of claim 8, wherein the database is selected from among the group: a blockchain, a distributed ledger technology, or a serialization database.

11. The device of claim 10, wherein the database information is displayed on a dashboard.

\* \* \* \* \*